United States Patent [19]
Cardoso

[11] Patent Number: 6,093,169
[45] Date of Patent: *Jul. 25, 2000

[54] NASAL OXYGEN CATHETER

[76] Inventor: Norman Cardoso, HCR 2, Box 972, Satsuma, Fla. 32189

[ * ] Notice: This patent issued on a continued prosecution application filed under 37 CFR 1.53(d), and is subject to the twenty year patent term provisions of 35 U.S.C. 154(a)(2).

[21] Appl. No.: 08/854,132

[22] Filed: May 8, 1997

[51] Int. Cl.[7] .................................................. A61M 11/00
[52] U.S. Cl. ........................... 604/94; 604/179; 604/180; 606/199; 128/207.18; 128/DIG. 26
[58] Field of Search ....................... 128/207.18, DIG. 26; 604/94, 174, 179, 180; 602/5, 17, 902; 606/199

[56] References Cited

U.S. PATENT DOCUMENTS

| 3,682,171 | 8/1972 | Dali et al. . |
|---|---|---|
| 4,782,832 | 11/1988 | Trimble et al. . |
| 5,535,739 | 7/1996 | Rapoport et al. . |
| 5,685,292 | 11/1997 | Fenn . |
| 5,735,272 | 4/1998 | Dillon et al. . |
| 5,752,511 | 5/1998 | Simmons et al. . |

FOREIGN PATENT DOCUMENTS 0229378  12/1910  Germany .

*Primary Examiner*—Mark Bockelman
*Attorney, Agent, or Firm*—Howard L. Rose

[57] ABSTRACT

A mounting structure for a nasal oxygen catheter elevates and somewhat shortens the tip of the nose of a user to increase the area of the nasal air passages whereby a large quantity of air may enter the nostrils and sweep oxygen into the nostrils with each inhalation of the user. In a preferred embodiment a cup-shaped member snubs the end of the nose and has preferably a plurality of downwardly extending fingers in contact with said catheter.

16 Claims, 2 Drawing Sheets

NASAL OXYGEN CATHETER

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to nasal oxygen catheters and more particularly to an improved nasal oxygen catheter retainer.

A standard oxygen catheter has two rigid hollow stubs that are inserted into the nostrils of a patient and retained by a harness that comprises two hollow tubes in a continuous loop connected to the source of oxygen. The tube (tubes) are looped over the ears of the user. The two tubes are connected to the source of oxygen and each supplies oxygen to the oxygen delivery stubs.

The problem with the above arrangement is that the stubs often become dislodged and delivery of oxygen to the patient is reduced or lost altogether. Further it is quite common for the stubs to barely enter the nostrils and the flow of oxygen into the nose is not greatly assisted by the flow of air during inhalation by the patient.

OBJECTS OF THE INVENTION

It is an object of the present invention to provide a structure for insuring that the stubs of a nasal oxygen catheter are retained in the nostrils of the nose of a patient.

It is another object of the present invention to provide a strut that supports the stubs of a nasal oxygen catheter and in use is secured to the nose of the patient.

It is yet another object of the present invention to employ a structure for securing the stubs of a nasal oxygen catheter in the nostrils and to slightly increase the caliber of the anterior nasal passage to facilitate the ingress of gases into the vestibule of the nose.

It is still another object of the present invention to employ a mounting structure for a nasal oxygen catheter that facilitates entry of gases into nasal passages by elevating and somewhat shortening the tip of the nose to increase the penetration of the delivery stubs and increase the area of the air passages of the nostrils.

Still another object of the present invention is to expand the area of the nostrils adjacent the entry region so that a large quantity of air may enter the nostrils and sweep oxygen into the nose.

BRIEF SUMMARY OF THE INVENTION

An L-shaped strut for securing the nasal oxygen catheter to the patient has the long leg of the L-shaped strut secured to the patient's nose by various means such as tape or a strut conformed to the specific configuration of the patient's nose. At its septal end a short end of the strut is secured to the outer surface of the oxygen catheter between the delivery stubs.

The short leg of the strut engages the tip of the nose and both elevates it slightly and shortens it. As the tip of the nose is elevated and shortened the resulting flaring of the anterior airways of the nostrils permits better ingress of the oxygen delivery stubs into the nose and increases the size of the airways surrounding these stubs. As external air is more easily drawn into the nostrils by inhalation, the oxygen being delivered by the stubs is more completely swept in with the air and into the lungs.

In a preferred embodiment of the invention the stubs that enter the nose are formed as direct extensions of a hollow cylinder that is formed integrally with the oxygen supply hose. The hose comes off of both sides of the hollow cylinder and can be looped over the ears of the user. An attachment structure includes an anchor to the nose which is secured to the cylinder and immediately adjacent the cylinder has a cup-shaped member that snubs the end of the nose to assist in shortening the length of the nose to cause the nostrils to flare.

Three fingers depend downwardly from the cup-shaped member to engage the forward surface of the cylinder to stabilize it.

The above and other features, objects and advantages of the present invention, together with the best means contemplated by the inventor thereof for carrying out the invention will become more apparent from reading the following description of a preferred embodiment and perusing the associated drawings in which:

DETAILED DESCRIPTION OF THE INVENTION

Figure 1:
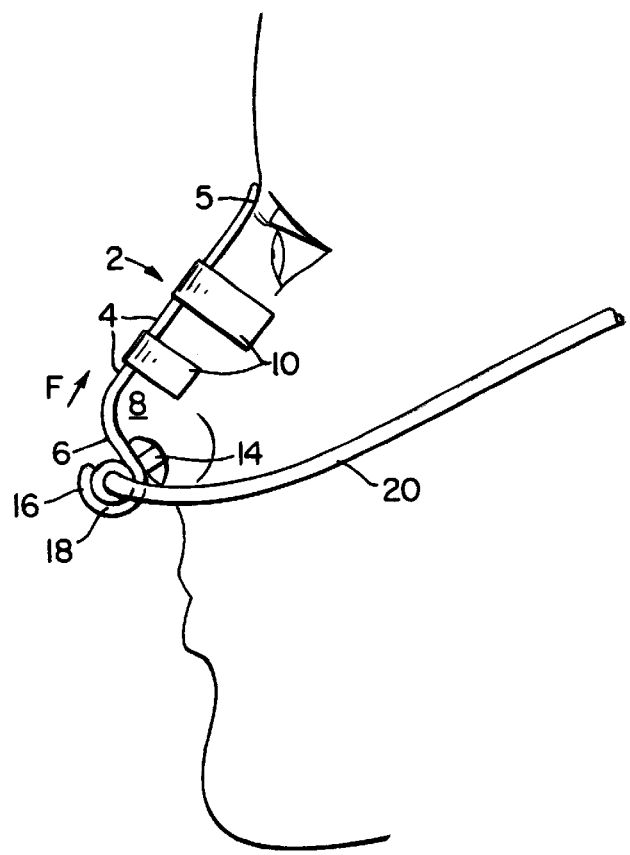
FIG. 1 is a side view of the strut of the present invention as applied to the nose of a patient.
Figure 2:
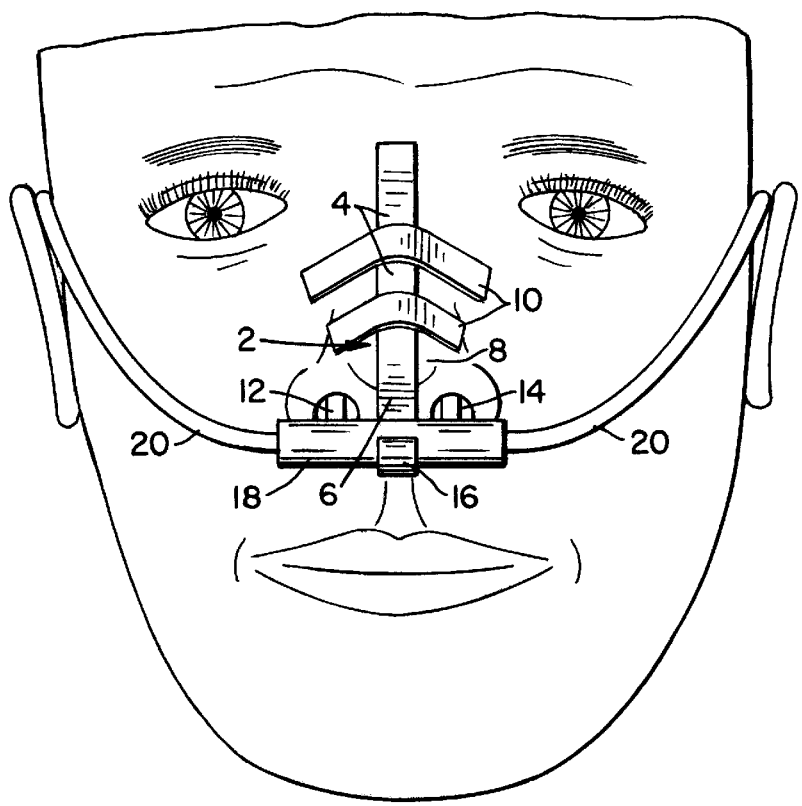
FIG. 2 is a top view looking down on the nose of the patient.

Referring now to FIG. 1 of the present invention, a generally L-shaped strut 2 has a long leg 4 and a short leg 6. The strut may be secured to the nose, generally designated by the reference numeral 8, of the patient by various means such as tape 10. In use with a patient under long term care, the long leg of the strut may be fabricated to conform to the shape of the patient's nose sufficiently to be retained thereon by contact. Preferably the strut should extend to the root of the nose designated by reference numeral 5.

The short leg 6 of the strut 2 passes under and curves around a short hollow rigid tube 18 between oxygen delivery stubs 12 and 14. The stubs are in flow communication with tube 18 that is in turn in flow communication with flexible oxygen delivery tubes 20. The tubes receive oxygen from a standard source of oxygen.

When the long arm 4 of the strut 2 is pulled toward the root of the nose and then fixed to the skin along the "ridge pole" either by being cross-taped or by having been made with self adhesive, the result is that the tip of the nose is pulled slightly inward and upward as traction is applied to the long arm of the strut. This action makes the tip of the nose move slightly inward toward the root of the nose.

It is to be noted that the upward tilt and shortening of the tip of the nose is not great but is sufficient to open the passages to produce a significant increase in the entry region of the nostrils. Accordingly, the volume of air inducted on each inhalation is increased relative to the norm for that individual and thus increases the quantity of the oxygen that would otherwise be carried by airflow.

It is apparent that the oxygen supply stubs are firmly held in place.

Figure 3:
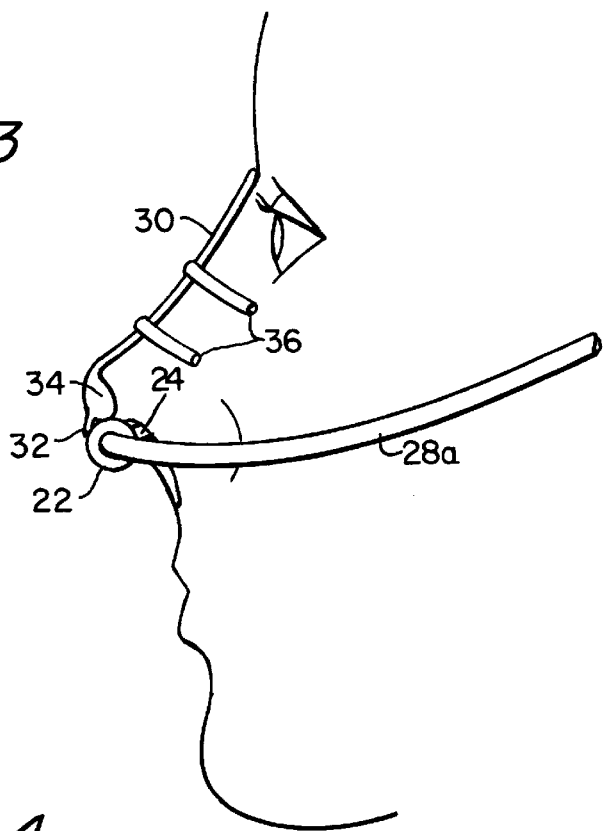
FIG. 3 is a side view of a preferred embodiment of the present invention.
Figure 4:
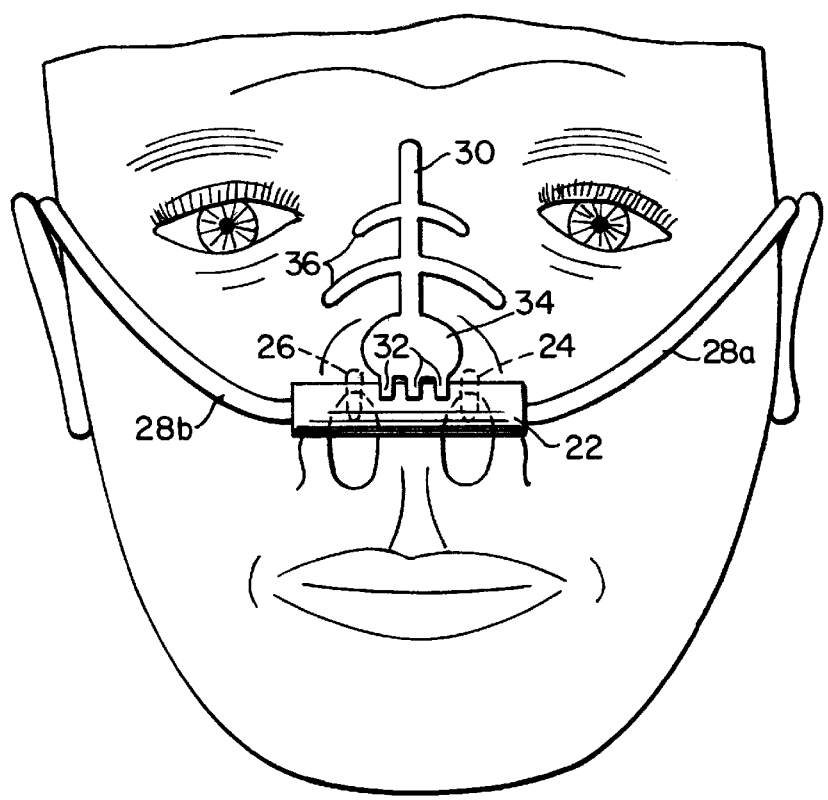
FIG. 4 is a front view of the preferred embodiment of the present invention.

Referring now to FIGS. 3 and 4 of the accompanying drawings, in this embodiment a hollow cylinder 22 has nasal stubs 24 and 26 which may be formed integrally with and are in fluid flow communication with the interior of the cylinder 22. The two ends of the cylinder 22 are molded together with hollow tubing 28a and 28b that are joined into a single hose that extends to a source of oxygen.

The cylinder 22 may be formed integrally with a nose strap 30 and three fingers 32 are molded with the nose strap and are employed to stabilize the cylinder 22, that is, to resist twisting thereof. The fingers 32 extend from a cup-shaped region 34 located at the end of the nose strap, and is intended to engage the end of the nose and retract it. The enlarged cup-shaped region 34, fits over the end of the nose above the nostrils and snubs the end of the nose raising the tip of the nose and pushing it back up the nose thus producing the desired flaring of the nostrils. The strap 30 has an adhesive on its underside where it contacts the nose of the user and is further secured to the nose of the user by tapes 36 also coated on their undersides by an adhesive.

It should be noted that the enlarged end region 34 extends down over the end of the nose providing an L-shaped member.

Various other arrangements of components and means for securing the device to the nose are available. For instance, the tapes may employ a reusable adhesive so that the catheter may be removed and reused a number of times or the adherent supporting structure may be made removable and re-attachable to the supported catheter and then may be replaced as necessary.

Once given the above disclosure, many other features, modifications and improvements will become apparent to the skilled artisan. Such features, modifications and improvements are, therefore, considered to be a part of this invention, the scope of which is to be determined by the following claims.

I claim:

1. A nasal catheter support structure comprising a generally L-shaped strut having a long leg and a short leg, a pair of hollow stubs for insertion into the nostrils of a user's nose, a hollow support for said stubs generally transverse to said stubs, said hollow support in flow communication with said stubs, said long leg of said L-shaped member securable to a nose of a user, said short leg secured to and supporting said hollow support, said long leg disposable on the user's nose in a position to cause the short leg to raise and shorten the tip of the nose of the user.

2. A nasal catheter support structure according to claim 1 wherein said long leg is constructed so that it may conform to the nose of the user and be taped to the nose of a user.

3. A nasal catheter support structure according to claim 1 wherein said long leg has a mastic on an undersurface of the structure to contact the nose of the user.

4. A nasal catheter support structure according to claim 1 further comprising means for connecting said hollow support in flow communication with a source of pressurized oxygen.

5. A nasal catheter support structure according to claim 1 further comprising means for connecting said hollow support in flow communication with a source of pressurized gas for treating an ailment.

6. A nasal catheter support structure according to claim 1 further comprising a cup-shaped region at the juncture of the short and long legs of said L-shaped strut positioned to be in engagement with the nose of the user said cup-shaped region extending laterally outward in both directions at from said juncture.

7. A nasal catheter support structure according to claim 6 further comprising means for resisting twist at said region.

8. A nasal catheter support structure according to claim 6 wherein said hollow support, said region and said strut are molded as a single structure.

9. A nasal catheter support structure according to claim 6 further comprising a plurality of finger like elements extending downwardly from said region into contact with said hollow support at laterally spaced apart regions of said hollow support.

10. A nasal catheter support structure according to claim 1 wherein said hollow support, said strut and said hollow stubs are molded as a single structure.

11. A nasal catheter support structure according to claim 10 wherein hollow tubes having means for connection to a source of gas are molded integrally in fluid flow communication with said hollow support each adjacent a different end of said hollow support.

12. A nasal catheter support structure according to claim 10 wherein at least one of said hollow tubes is sufficiently long to extend over an ear of the user.

13. A nasal catheter support structure according to claim 10 further comprising two said hollow support are long enough to extend over the ears of the user.

14. A device for attachment to an elongated member comprising a structure having a long leg and a short leg, said long leg having a length less than the length of the elongated member, said short leg having a predetermined length, said legs lying generally at angles to one another, a cup shaped laterally expanded region relative to said legs formed at the juncture of the legs; and means for delivering fluids to the patient attached to the short leg.

15. A device according to claim 14 for attachment to the nose of a user further comprising members extending at right angles to said long leg and engaging the sides of the nose.

16. A device according to claim 14 for attachment to the nose of a user further comprising means for attaching the device to the nose of the user in such a fashion as to pull up on the end of the user's nose.

* * * * *